United States Patent [19]

Hajos et al.

[11] Patent Number: 5,252,569
[45] Date of Patent: Oct. 12, 1993

[54] 6-SUBSTITUTED PURINYL PIPERAZINE DERIVATIVES

[75] Inventors: Zoltan G. Hajos, Princeton; Jeffery B. Press, Rocky Hill, both of N.J.

[73] Assignee: Ortho Pharmaceutical Corporation, Raritan, N.J.

[21] Appl. No.: 859,597

[22] Filed: Mar. 23, 1992

Related U.S. Application Data

[63] Continuation of Ser. No. 527,625, May 23, 1990, abandoned.

[51] Int. Cl.$^5$ .................. C07D 245/02; C07D 295/08; C07D 241/02; C07D 239/70
[52] U.S. Cl. .................................... 514/212; 514/218; 514/253; 514/262; 514/266; 540/482; 540/575; 544/276; 544/277
[58] Field of Search .................. 544/276, 265, 277; 540/492, 524, 482, 575; 514/212, 218, 262, 253, 266

[56] References Cited

U.S. PATENT DOCUMENTS 4,234,583 11/1980 Buending et al. .................. 424/250
4,876,257 10/1989 Hajos et al. .......................... 514/253

OTHER PUBLICATIONS

Fessenden and Fessenden, "Organic Chemistry, 2nd ed." 1982 p. 616.

*Primary Examiner*—Mukund J. Shah
*Assistant Examiner*—Matthew V. Grumbling

[57] ABSTRACT

Novel 6-substituted purinyl piperazine derivatives are described. The novel derivatives are useful as cardiotonic agents and antiarrhythmic agents.

21 Claims, No Drawings

6-SUBSTITUTED PURINYL PIPERAZINE DERIVATIVES

This is a continuation of application Ser. No. 527,625, filed May 23, 1990 now abandoned.

BACKGROUND OF THE INVENTION

1. Field of the Invention

The present invention relates to compounds of the formula:

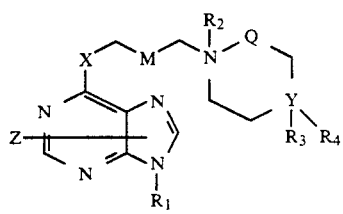

as further described herein. These compounds are useful as cardiovascular agents. The compounds possess positive ionotropic activity and are especially useful as cardiotonic agents for improving cardiac ejection, particularly in the setting of acute or chronic heart failure. The compounds are also useful as antiarrhythmic agents for the treatment or prevention of cardiac arrythmias.

DESCRIPTION OF THE PRIOR ART

British Patent Application No. GB2186573 and German Patent Application No. DE3703633 relate to purine derivatives possessing cardiotonic and antiarrhythmic activity and having the following formula:

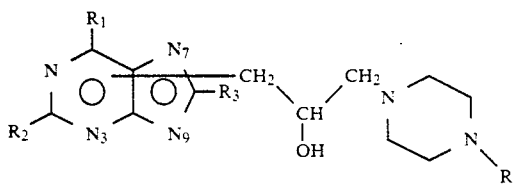

wherein R is an preferably unsubstituted diphenyldialkyl group. The side chain in the above formula is bonded to a ring nitrogen atom (3, 7 or 9) but not to $R_1$, $R_2$ or $R_3$.

U.S. Pat. No. 4,460,586 relates to 3-aminopropoxyaryl derivatives of the formula:

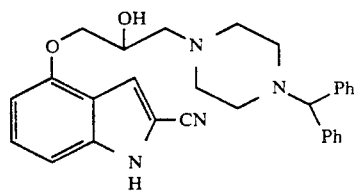

These compounds are useful as cardiotonic, antiarrhythmic and α- and β-adrenoceptor blocking agents. This U.S. patent is one of a series of patents that have issued claiming various 4-substituted indole derivatives.

U.S. Pat. No. 3,919,226 describes purine compounds of the formula:

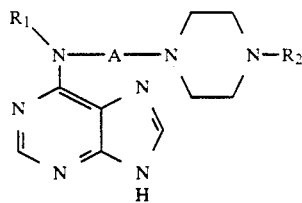

wherein $R_1$ is hydrogen or lower alkyl; $R_2$ is phenyl or benzyl, optionally substituted by halogen, lower alkyl or lower alkoxy; and A is lower alkylene optionally substituted by a hydroxyl group. These compounds have anti-edema, anti-inflammatory and anti-allergic activity.

SUMMARY OF THE INVENTION

The present invention is directed to 6-substituted purinyl piperazine derivatives of the general formula:

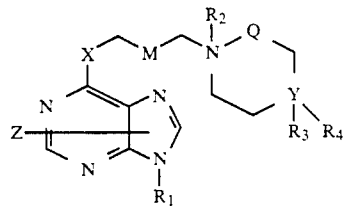

wherein $R_1$ may be hydrogen, $C_1$–$C_4$ lower alkyl, cyclopentyl, cyclohexyl, benzyl, $C_2$–$C_6$ lower alkenyl, $C_2$–$C_6$ lower alkynyl, tetrahydropyranyl or tetrahydrofuranyl;

$R_2$ and $R_3$ are the same or different, and may be no substituent or oxygen;

$R_4$ may be naphthyl, pyridyl, thienyl, $CHR_5R_6$, or $CR_5R_6$ when Y is C=, phenyl or substituted phenyl wherein the substituent may be $C_1$–$C_4$ lower alkyl, $C_1$–$C_4$ lower alkoxy, $CF_3$, halo, perhalo, $NO_2$ or CN;

$R_5$ and $R_6$ are the same or different and may be pyridyl, thienyl, phenyl or substituted phenyl wherein the substituent is $C_1$–$C_4$ lower alkyl, $C_1$–$C_4$ lower alkoxy, $CF_3$, halo, perhalo, $NO_2$ or CN;

Z may be hydrogen, CN, $C_1$–$C_4$ lower aklyl, halo, hydroxy, amino or $CO_2R_7$ wherein $R_7$ may be hydrogen, $C_1$–$C_4$ lower alkyl, phenyl or substituted phenyl wherein the substituent may be $C_1$–$C_4$ lower alkyl, $NO_2$, halo, CN or $CF_3$;

X may be S, O, NH or $NR_8$ wherein $R_8$ is $C_1$–$C_4$ lower alkyl;

M may be $CH_2$, CHOH, $CHOCOR_9$ or $CHOR_9$ wherein $R_9$ may be straight or branched chain $C_1$–$C_8$ lower alkyl, $SO_3H$, phenyl or substituted phenyl wherein the substituent on the phenyl ring may be $C_1$–$C_4$ lower alkyl, $CF_3$, halo, $C_1$–$C_4$ lower alkoxy, $NO_2$ or CN;

Q may be $CH_2$ or $(CH_2)_2$; and

Y may be nitrogen, or a carbon atom having a double bond (C=) when $R_4$ is $CR_5R_6$;

with the provisos that:

(a) when Y is N and $R_4$ is any substituent other than $CR_5R_6$, X is S or O;

(b) when $R_4$ is $CHR_5R_6$ or $CR_5R_6$, $R_2$ and/or $R_3$ are oxygen, and/or Q is $(CH_2)_2$; and (c) when $R_4$ is $CHR_5R_6$ or $CR_5R_6$, at least one of $R_5$ and $R_6$ is an aromatic group.

Also included in the present invention are the optically active isomers of these 6-substituted purinyl piperazine derivatives.

The compounds of the general formula are useful as cardiovascular agents in mammals, and in particular as cardiotonic agents, and are also useful as antiarrhythmic agents.

DETAILED INVENTION OF THE INVENTION

The invention in its broadest aspects relates to 6-substituted purinyl piperazine derivatives which exhibit positive inotropic activity.

The compounds of the present invention wherein X is sulfur can be prepared as outlined in Scheme 1.

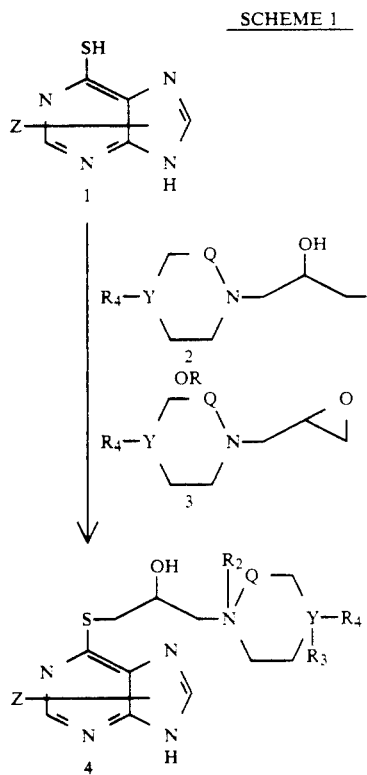

In this Scheme, an appropriately substituted 6-mercaptopurine derivative 1 is treated with a base such as an amine (for example, triethylamine), a metal hydroxide (for example, sodium or potassium hydroxide), or a metal hydride (for example, sodium hydride) in an inert solvent such as dimethylformamide (DMF) or tetrahydrofuran (THF). The anion formed is then reacted with an appropriately substituted alkylating agent such as the chloride 2 or the epoxide 3 and the reactants are allowed to react for about 2 to 200 hours at a temperature of about 0° to 100° C. to form the compounds of the invention 4. In order to obtain the inventive compounds 4 in which $R_2$ and/or $R_3$ are oxygen (i.e. N-oxides), the compound 4 is reacted with m-chloroperoxybenzoic acid. The chlorides 2 and epoxides 3 used as the alkylating agents are either commercially available or they can be prepared by procedures found in the chemical literature and available to those skilled in the art.

Alternatively, the compounds of the present invention wherein X is sulfur (S), NH, $NR_8$ or oxygen (O) can be prepared by the procedure outlined in Scheme 2.

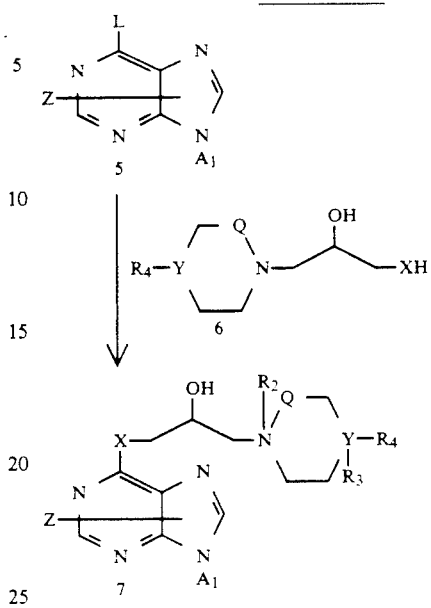

An appropriately substituted purine 5 having a suitable leaving group (L) in the 6-position on the six membered ring is reacted with an appropriately substituted alcohol 6 where X is oxygen, with an amine where X is NH or $NR_8$, or with a mercaptan where X is sulfur, in a suitable solvent such as benzene, toluene, DMF, dimethylsulfoxide (DMSO) or THF, for example. Examples of a suitable leaving group (L) include a chloro, brono or tosyl group.

The purine starting material 5 may or may not be substituted at the N-9 position ($R_1$). The reaction may be carried out in the presence of a base and/or a catalyst. Suitable bases which can be employed include alkali metal and alkaline earth metal hydroxides and hydrides such as sodium or potassium hydroxide, and sodium or potassium hydride, and sodium or potassium metal.

The reaction may also be carried out in the presence of a phase transfer or a crown ether catalyst such as 18-crown-6, for example. When the group at N-9 ($R_1$) is a protecting group it can be removed by acid (in the case where $R_1$ is tetrahydropyranyl or tetrahydrofuranyl) or hydrogenolysis (in the case where $R_1$ is benzyl).

The compounds of the invention 7 may also be reacted with m-choloperoxybenzoic acid in order to obtain N-oxides (i.e. $R_2$ and/or $R_3$ are oxygen).

The compounds of the present invention can also be prepared as outlined in Scheme 3.

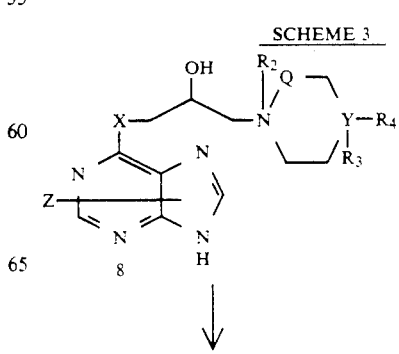

-continued
SCHEME 3

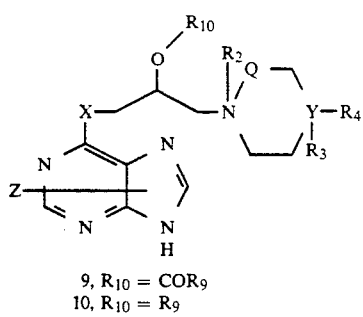

9, $R_{10}$ = $COR_9$
10, $R_{10}$ = $R_9$

An appropriately substituted alcohol 8 is reacted with an acid chloride, such as acetyl chloride or propionyl chloride, for example, or the corresponding acid anhydride, in the presence of a base such as, for example, triethylamine or pyridine. This reaction takes place in a suitable solvent such as THF or methylene chloride, for example, to form the ester derivative 9 ($R_{10}$ is $COR_5$ wherein $R_5$ is as defined above).

If an alkyl iodide such as methyl iodide, for example, is employed as the alkylating agent, the reaction is generally carried put in the presence of a strong base such as sodium hydroxide or sodium hydride, for example, to form the ether derivatives 10 ($R_8$=$R_5$ wherein $R_5$ is as defined above). In those cases where $R_1$ is tetrahydropyranyl, for example, the protecting group may be removed by hydrolysis with mild acid such as dilute hydrochloric acid.

The compounds of the present invention wherein X is sulfur can also be prepared as outlined in Scheme 4.

SCHEME 4

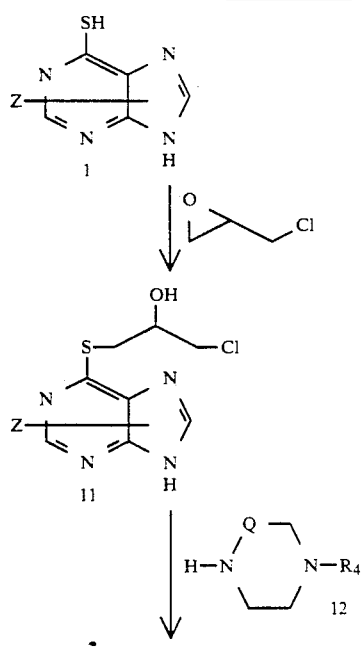

-continued
SCHEME 4

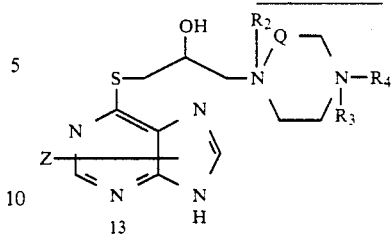

In this procedure, an appropriately substituted 6-mercapto-purine derivative 1 is treated with epichlorohydrin or glycidyl tosylate in either its racemic or optically active [(2R)-(−) or 2S-(+))] form in a suitable solvent, such as ethanol, acetonitrile, DMF or DMSO. The reaction is carried out at a temperature of about 0°–50° C. for a period of about several hours to about 10 days to give the chloride derivative 11. The reaction may optionally be carried out in the presence of a base such as sodium bicarbonate.

Treatment of the chloride derivative 11 with an appropriately substituted benzhydryl piperazine or homopiperazine 12 either neat or in the presence of a solvent at a temperature of about 15°–50° C. for from about several hours to several weeks results in the purinyl piperazine derivative 13 as a racemic or optically active form. Suitable solvents which can be employed in the reaction include methanol, ethanol, DMF and DMSO.

The purinyl piperazine derivative 13 may also be reacted with m-chloroperoxybenzoic acid to yield N-oxides of compound 13 (i.e. $R_2$ and/or $R_3$ oxygen).

The benzhydryl piperazine and homopiperazine compounds 12 are available commercially or they can be prepared according to literature procedures known to those skilled in the art.

Unsymmetrical biaryl compounds ($R_4$ is $CHR_5R_6$ and $R_5$ and $R_6$ are aryl groups) may be prepared by reacting an aromatic carboxylic acid derivative such as ethyl 2-naphthalenecarboxylate with an organometallic reagent such as 2-pyridyl lithium under controlled conditions to give 2-naphthyl 2-pyridyl ketone. This ketone may then be reacted with an organometallic reagent such as 2-thienyl lithium to give 1-(2-naphthyl)-1-(2-pyridyl)-1-(2-thienyl)methanol. This alcohol may in turn be reacted with a halogenating agent such as thienyl chloride to give the corresponding chloromethane derivative in a manner similar to that described in Procedure 12 below. Reaction with a piperazine or homopiperazine in a like manner as described in Procedure 12 gives the requisite piperazine or homopiperazine derivative. By varying the aromatic carboxylic acid derivative and the choice of the organometallic reagents in this procedure, a variety of bis-unsymmetrical benzhydryl piperazine and homopiperazine derivatives may be prepared.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included; injectable suspensions may also be prepared, in which case appropriate liquid carriers, suspending agents and the like may be employed. The pharmaceutical compositions will generally contain a dosage per unit, e.g., tablet, capsule, powder, injection, teaspoonful and the like, from about 0.01 to about 50 mg/kg, and preferably from about 0.1 to about 10 mg/kg of the active ingredient.

The following examples describe the invention in greater particularity and are intended to be a way of illustrating but not limiting the invention. Some of the compounds in the examples were obtained as the hydrate. The water can be removed from the hydrates by drying at temperatures below the melting point of the compound.

EXAMPLE 1

6-[1-[1-Bis(4-fluoroethyl)methyl]piperazin-4-yl]-2-hydroxy-3-propanylthio]purine Hemihydrate To DMF (7 mi), 6-mercaptopurine (5 mmol, 0.85 g) was added in portions and the solution was stirred at room temperature, under $N_2$ for 5 minutes. $Et_3N$ (5 mmol, 0.69 mL) was added dropwise. After 5 minutes, 1-(1-chloro-2-hydroxy-3-propanyl)-4-[bis(4-fluorophenyl)methyl]-piperazine (5 mmol, 1.9 g) in DMF (5 mL) was added dropwise over 5 minutes at room temperature under $N_2$. After 22 hours, the solution was filtered through a sintered glass funnel and the filtrate was evaporated (1.0 mm Hg, 50° C., stirring). Silica gel flash chromatography of the crude product (2.34 g) using 10% $MeOH:CH_2Cl_2$ gave pure product, 0.630 g (25.44), mp 115°–116° C. (dec). DCI/MS (M+1) 497. 400 MHz $^1H$ NMR ($CDCl_3$) δ: 8.6 (s, 1H), 8.25 (s, 1H), 7.35 (m, 4H) 6.95 (m, 4H), 4.2 (s, 1H), 4.15 (m, 1H), 3.45 ad 3.6 (m, 2H), 2.65 (m 2H), 2.6 (m, 4H), 2.4 (m,4H).

Anal. Calcd. for $C_{25}H_{26}F_2N_6OS.\frac{1}{2}$ $H_2O$: C, 59.40; H, 5.38; N, 16.62 Found: C, 58.88; H, 5.34; N, 16.56.

EXAMPLE 2

6-[1-[1-Bis(4-fluorophenyl)methyl]piperazin-4-yl]-2-hydroxysulfonyloxy-3-propanylthio]purine.0.75 Hydrate To 6-[1-[1-bis(4-fluorophenyl)methyl]piperazin-4-yl]-2-hydroxy-3-propanylthio]purine hemihydrate (1.5 g, 3 mmol) from Example 1, dissolved in methylene chloride (10 mL), was added triethylamine (0.3 mL) at room temperature. The mixture was cooled to −15° C., and chlorosulfonic acid (1.5 mL) in methylene chloride was added dropwise with stirring over a period of 10 minutes. After stirring for 1 hour at −15° C., the mixture was warmed to room temperature and stirred overnight. The resultant precipitate was collected by filtration and washed with methylene chloride (10×20 mL) to give a solid(1.65 g). Trituration in pentane, refiltration and drying in vacuo at 50° C. gave the title compound, 1.34 g (75%), mp 197°–202° C. FAB/MS (M+1) 497. 300 MHz $^1H$ NMR ($CDCl_3$) δ: 8.69 (s, 1H), 8.47 (s, 1H), 7.44 (m, 4H), 7.16 (m, 4H), 4.59 (m, 1H), 4.30 (d, 1H), 3.43–3.80 (m, 6H), 3.20 (m, 2H) 2.77 (m, 2H), 2.36 (m, 2H).

Anal. Calcd. for $C_{25}H_{26}F_2N_6O_4S_2.0.75$ $H_2O$: C, 50.88; H, 4.70; N, 14.24 Found: C, 50.99; H, 4.83; N, 14.24.

EXAMPLE 3

6-[1-[1-[Bis(4-fluorophenyl)methyl]piperazin-4-yl]-2-acetoxy-3propanylthio]purine ¼ Hydrate To a solution of 6-[1-[1-[bis(4-fluorophenyl) methyl]-piperazin-4-yl)-2-hydroxy-3-propanylthio]purine (1.0 g, 0.002 mol) from Example 1, in $CH_2Cl_2$ (7 mL), acetic anhydride (0.2 mL, 0.002 mol) , $Et_3N$ (0.2 mL, 0.002 mol) was added dropwise over 5 minutes at room temperature under nitrogen. After 70 hours, $CH_2Cl_2$ (50 mL) was added, and the solution was extracted with saturated $NaHCO_3$ (2×100 mL), $H_2O$ (1×100 mL), and saturated brine (1×100 mL); the organic layer was dried over $Na_2SO_4$. Solvent removal of the dried organic layer gave a solid which was dried in vacuo at 40° C. to give pure product (0.7 g, 64.8%), mp 105°–109° C. (dec). DCI/MS (M+1) 539. 400 MHz $^1H$ NMR ($CDCl_3$) δ: 8.7 (s, 1H), 8.2 (s, 1H), 7.3 (m, 4H), 6.95 (m, 4H), 5.3 (m, 1H), 4.2 (s, 1H), 3.4 and 4.0 (m, 2H), 2.65 (m, 2H), 2.6 (m, 4H), 2.4 (m, 4H), 2.0 (s, 3H).

Anal. Calcd. for $C_{27}H_{28}F_2N_6O_2S.0.75$ $H_2O$: C, 58.74; H, 5.38; N, 15.22 Found: C, 58.69; H, 5.37; N, 15.02.

EXAMPLE 4

6-[1-[1-[Bis(4-fluorophenyl)methyl]piperazin-1-N-oxide-4-yl]-2-acetoxy-3-propanylthio]purine Monohydrate To 6-[1-[1-bis(4-fluorophenyl)methyl)piperazin-4-yl]-2-acetoxy-3-propanylthio]purine (1.1 g, 2.0 mmole) from Example 3, dissolved in methylene chloride (10 mL), was added with stirring at 0° C. m-chloroperoxybenzoic acid (400 mg, 2 mmol of 85% pure) dissolved in methylene chloride (10 mL), over 30 minutes. The mixture changed from yellow to almost colorless and gave a negative peroxide test. The mixture was then washed with saturated aqueous sodium bicarbonate (2×50 mL) and saturated brine, and dried with sodium sulfate. Filtration and evaporation in vacuo gave the title compound (1.04 g, 100%) as a light beige solid, mp 144°–145° C. (dec.). IR (KBR) 1743 $cm^{-1}$; 300 Mc $^1H$ NMR ($CDCl_3$) δ: 8.00 (s, 1H), 7.91 (s, 1H), 7.27 (m, 4H), 6.98 (m, 4H), 5.94 (m, 1H), 4.32 (s, 1H), 3.9 (m, 2H), 2.6–3.9 (m, 10H), 2.11 (s, 3H), FAB/POS/LOWRES MS M+1=555 (BP).

Anal. Calcd. for $C_{27}H_{28}F_2N_6O_3S.H_2O$: C, 56.63; H, 5.28; N, 14.67 Found: C, 56.69; H, 5.08; N, 14.11.

EXAMPLE 5

6-[1-[1-Bis(4-fluorophenyl)methyl]piperazin-1-N-oxide-4-yl]-2-hydroxy-3-propanylthio]purine Monohydrate To 6-[1-[1-bis(4-fluorophenyl)methyl)piperazin-1-N-oxide-4-yl]-2-acetoxy-3-propanylthio]purine monohydrate (0.7 g, 1.2 mmol) from Example 4, in methanol (7 mL) was added dry sodium bicarbonate (0.3 g, 3.6 mmol). The suspension was stirred at room temperature for 24 hours and was filtered through a medium sintered glass funnel. The filtrate was evaporated in vacuo to give an oil (1.3 g) which was triturated with methylene chloride and re-evaporated to give a white solid (0.75 g). The solid was purified by silica gel flash chromatography using 15% methanol/methylene chloride to give the title compound (0.134 g, 55%), a white solid, mp 155°-157° C. (dec). 300 MHz$^1$H NMR (DMSO-$d_6$) δ: 8.31 (s, 1H), 7.80 (s, 1H), 7.4 (m, 4H), 7.12 (m, 4H), 4.54 (s, 1H), 4.41 (m, 1H), 3.05-3.40 (m, 10H), 2.5-2.7 (m, 2H), FAB/POS/LOWRES MS (M+1)=513 (BP).

Anal. Calcd. for $C_{25}H_{26}F_2N_6O_2S.H_2O$: C, 56.59; H, 5.32; N, 15.84 Found: C, 56.82; H, 5.05; N, 15.82.

EXAMPLE 6

6-[1-[1-[Bis(4-fluorophenyl)methyl]piperazin-4-N-oxide-4-yl]-2-hydroxy-3-propanylthio]purine Hydrate To 6-[1-[1-[bis(4-fluorophenyl)methyl]piperazin-4-yl]-2-hydroxy-3-propanylthio]purine hemihydrate (1.98 g, 3.9 mmol) from Example 1, dissolved in methylene chloride (15 mL) was added m-chloroperoxybenzoic acid (800 mg, 4.1 mmol) dissolved in methylene chloride (15 mL) with stirring at 0° C. The addition took approximately 30 minutes. The reaction mixture was washed with saturated aqueous sodium bicarbonate (2×50 mL) and saturated brine (50 mL), and filtered. The collected precipitate was washed with methylene chloride to remove colored impurities and dried to give a white solid, 1.53 g. A 700 mg portion of this solid was suspended in methylene chloride (20 mL) and water (20 mL) and the mixture was stirred vigorously for 30 minutes. The suspension was filtered, washed with water (3×20 mL) and methylene chloride (4×25 mL) and dried at room temperature in vacuo to give the title compound, mp 150°-152° C. 300 MHZ$^1$H NMR (DMSO-$d_6$) δ: 8.8 (s, 1H), 8.4 (s, 1H), 7.0-7.4 (m, 8H), 4.6 (s, 1H), 4.55 (m, 1H), 3.5 (m, 2H), 3.0-3.4 (m, 10H), FAB/POS/LOWRES MS (M+1)=513 (BP).

Anal. Calcd. for $C_{25}H_{26}F_2N_6O_2S.H_2O$: C, 56.59; H, 5.32; N, 15.84 Found: C, 56.82; H, 5.05; N, 15.82.

EXAMPLE 7

6-[1-[1-[Bis(4-fluorophenyl)methyl]homopiperazine-4-yl]-2-acetoxy-3-propanylthio]purine Hemihydrate To 6-mercaptopurine (5 mmol, 0.85 g) in DMF (7 mL) with Et$_3$N (0.7 mL, 5 mmol) was added at room temperature 1-(1-chloro-2-hydroxy-3-propanyl)-4-(4,4'-difluorobenzhydryl)homopiperazine (1.97 g, 5 mmol) in DMF (15 mL) dropwise over 15 minutes, under nitrogen. After ten days, NaCl was removed by filtration and the solvent evaporated to give the crude product which was triturated with methylene chloride and the insoluble portion removed by filtration through Celite®. The filtrate was concentrated in vacuo to give a crude product (1.78 g). Silica gel flash chromatography using 20% methanol:methylene chloride gave product containing 6-mercaptopurine (400 mg) as a nice, white powder. To remove the 6-mercaptopurine, the crude product (flashed) was acetylated as follows.

To 6-[1-[1-bis(4-fluorophenyl)methyl]homopiperazin-4-yl]-2-hydroxy-3-propanylthio]purine (0.26 g, 0.51 mmol) (the filtrate from above) in methylene chloride (2 mL) was added acetic anhydride (0.05 mL, 0.51 mmol) in Et$_3$N (0.07 mL, 0.51 mmol) at room temperature under a nitrogen atmosphere. After three days, the solution was filtered and the filtrate extracted with aqueous saturated sodium bicarbonate (2×50 mL), water (1×50 mL) and saturated brine (1×50 mL), and dried over Na$_2$SO$_4$. Evaporation of the solvent gave a white solid (390 mg). After several washings with pentane, the solid was dried in a vacuum oven for 4 days to give pure product (0.160 g, 56.8%) as a white solid, mp 88°-90° C. (dec). DCI/MS (M+1) 553; 300 MHZ$^1$H NMR (CDCl$_3$) δ: 8.7 (s, 1H), 8.1 (s, 1H), 7.3 (m, 4H), 6.95 (m, 4H), 5.3 (m, 1H), 4.1 and 3.45 (q of q, 2H), 2.6-2.8 (m, 10H), 2.0 (s, 3H), 1.75 (m, 2H).

Anal. Calcd. for $C_{28}H_{30}F_2N_6O_2S.H_2O$: C, 59.88; H, 5.56; N, 14.96 Found: C, 59.86; H, 5.24; N, 14.61.

EXAMPLE 8

6-[1-[1-[2-Pyridyl]piperazin-4-yl]-2-acetoxy-3-propanylthio]purine Hemihydrate

To NaH (0.48 g, 10 mmol, pentane washed and decanted), in DMF (20 mL), was added at 0° C. in portions 6-mercaptopurine (1.70 g, 10 mmol). After 1.5 hours stirring at 0° C. under a nitrogen atmosphere, 1-(1-chloro-2-hydroxy-3-propanyl)-4-(2-pyridyl)piperazine (2.56 g, 10 mmol) was added in DMF (30 mL) dropwise over 5 minutes under nitrogen. After six days the DMF was removed in vacuo to give an opaque solid. Silica gel flash column chromatography with both 10% and 15% methanol:methylene chloride failed to separate the product from 6-mercaptopurine. To the crude mixture (2.94 g, 7.9 mmol) in methylene chloride (10 mL) was added acetic anhydride (0.8 mL, 7.9 mmol) in Et$_3$N (1.10 mL, 7.9 mmol) dropwise under nitrogen. After 17 hours, the mixture was extracted with water (1×50 mL) and saturated aqueous sodium bicarbonate (1×50 mL). Evaporation of the solvent gave 9.20 g of a residue. Silica gel flash column chromatography using 10% methanol:methylene chloride gave pure product as a white solid (0.57 mg, 17.43%). mp 66°-68° C. (dec). DCI/MS (M+1) 414. 300 MHZ$^1$H NMR (CDCl$_3$) δ: 8.85 (s, 1H), 8.2 (s, 1H), 8.2 (m, 1H), 7.5 (m, 1H), 6.65 (m, 1H), 5.45 (m, 1H), 3.5 and 4.1 (q of q, 2H), 3.55 (m, 4H) 2.7 (m, 6H) 2.0 (s, 3H).

Anal. Calcd. for $C_{19}H_{23}N_7OS.H_2O$: C, 54.01; H, 5.72; N, 23.21 Found: C, 54.00; H, 5.35; N, 22.97.

When in the above procedure, 1-(1-chloro-2-hydroxy-3-propanyl)-4-benzylpiperazine is used in place of 1-(1-chloro-2-hydroxy-3-propanyl)-4-(2-pyridyl)piperazine, 6-[1-[1-benzylpiperazin-4-yl]-2-acetoxy-3-propanylthio]purine hemihydrate is obtained.

Alternatively, when in the procedure of Example 8, 1-(1-chloro-2-hydroxy-3-propaynl)-4-piperonylpiperazine is used in place of I-(1-chloro-2-hydroxy-3-propanyl)-4-(2-pyridyl)piperazine, 6-[1-[1-piperonylpiperazin-4-yl]-2-acetoxy-3-propanylthio]purine hemihydrate is obtained.

EXAMPLE 9

6-[1-[1-[2-Pyridyl)piperazin-4-yl]-2-hydroxy-3-propanylthio]purine Monohydrate

To 6-[1-[1-[2-pyridyl)piperazin-4-yl]-2-acetoxy-3-propanylthio]purine (0.30 g, 0.725 mmol) from Example 8, in methanol (5 mL), was added anhydrous sodium bicarbonate (0.10 g, 0.725 mmol) at room temperature. After one week the methanol was removed in vacuo to give the crude product as a white solid. Silica gel flash chromatography using 10% methanol:methylene chloride gave the pure product as a white solid (0.260 g, 96.6%). mp 159°-161° C. DCI/MS (M+1) 372. 300 MHz$^1$H NMR (DMSO-$d_6$ and D$_2$O) δ: 8.6 (s, 1H), 8.4 (s, 1H), 8.1 (m, 1H), 7.5 (m, 1H) 6.8 (d, 1H, J=8.59 Hz), 6.6 (m, 1H), 4.0 (m, 1H), 3.3 and 3.7 (q of q, 2H), 2.5 (m, 10H).

Anal. Calcd. for $C_{17}H_{21}N_7OS \cdot H_2O$: C, 52.42; H, 5.95; N, 25.18 Found: C, 52.18; H, 5.61; N, 25.71.

EXAMPLE 10

6-[1-[1-(2-Methoxyphenyl)piperazin-4-yl]-2-acetoxy-3-propanylthio]purine

A.

1-(1-Chloro-2-hydroxy-3-propanyl)-4-(2-methoxyphenyl)piperazine

To epichlorohydrin (3.9 ML, 50 mmol) in $CH_3CN$ (3 mL) at 0° C. was added 1-(2-methoxyphenyl)piperazine (9 mL, 50 mmol) in $CH_3CN$ (20 mL) dropwise over 5 minutes under a nitrogen atmosphere. After 16 hours the resultant white precipitate was filtered away, washed with $CH_3CN$ and acetone, dried at 30° C. in a vacuum oven and identified as pure product (7.28 g, 51.1%). mp 96°-98° C. DCI/MS M+1=285. (100 MHz) 1 H nmr (dmso-d$_6$) δ:6.9 (m, 4H), 3.76, (m, 1H), 3.76 (s, 3H), 3.62 (d of d, 2H), 2.96 (m, 4H), 2.56 (m, 6H).

Anal. Calc'd. for $C_{14}H_{12}ClN_2O_2$: C, 59.04, H, 7.43, N, 9.84. Found: C, 59.40, H, 7.60, N, 10.54.

B.

6-[1-(1-(2-Methoxyphenyl)piperazin-4-yl]-2-acetoxy-3-propanylthio]purine

To 6-mercaptopurine (0.85 g, 5 mmol) dispersed in DMSO (10 mL) was added triethylamine (0.5 mL, 5 mmol). The mixture was heated to 45° C. and stirred for ½ hour. A solution of 1-(1-chloro-2-hydroxy-3-propanyl)-4-(2-methoxyphenyl)piperazine (1.42 g, 5 mmol) in methylene chloride (7 mL) was added and the mixture was stirred under nitrogen for 4 days. An additional equivalent of triethylamine (0.5 mL, 5 mmol) was added. After an additional 3 days, the solvent was removed in vacuo (0.5 mmHg, 70° C.). The residue was treated with methylene chloride (10 mL) and the mixture was filtered. The solid portion (1.23 g, 3.1 mmol) was stirred in methylene chloride (5 mL) with triethylamine (0.45 mL, 3.2 mmol) and acetic anhydride (0.30 mL, 3.2 mmol) at room temperature for 2 days. The solvent was removed in vacuo and the solid residue passed through a silica gel column using 10% methanol:methylene chloride to give the corresponding O-acetate (0.49 g, 35.8%). The ester was saponified by stirring the solid in methanol (5 mL) with anhydrous sodium bicarbonate (0.2 g, 2 mmol) for 3 days. The methanol was removed in vacuo and the solid stirred in water (10 mL) to remove the sodium bicarbonate. The mixture as filtered and the solid washed with pentane (2×10 mL) and methylene chloride (2×10 mL) and dried in a dessicator under reduced pressure for 24 hours to give the pure product (300 mg, 15.0%). mp 211°-212° C. (dec). DCI/MS (M+1) 401. 300 MHZ $^1$H NMR (DMSO-d$_6$) δ: 8.7 (s, 1H), 8.45 (s, 1H), 6.95 (m, 4H), 4.0 (m, 1H), 3.8 (s, 3H), 3.3 and 3.7 (q of q, 2H), 2.65 (m, 2H), 2.5 (m, 8H).

Anal. Calcd. for $C_{19}H_{24}N_6O_5S \cdot \frac{1}{2} H_2O$: C, 56.17; H, 6.14; N, 20.56 Found: C, 56.14; H, 6.12; N, 20.67.

When in the above procedure, 1-(1-chloro-2-hydroxy-3-propanyl)-4-(4-chlorobenzhydryl)piperazine hemihydrate is used in place of 1-(1-chloro-2-hydroxy-3-propanyl)-4-(2-methanoxyphenyl)piperazine, 6-[1-[1-(4-chlorobenzhydryl)piperazin-4-yl]-2-hydroxy-3-propanylthio]purine is obtained.

EXAMPLE 11

Cardiotonic Activity

Adult mongrel dogs were anesthetized with sodium pentobarbital (45 mg/kg, i.p.) and artificially respired. Mean arterial pressure (MAP) was recorded into a cannulated femoral artery and drugs were infused into a cannulated femoral vein. The arterial pressure pulse was used to trigger a cardiotachometer for determination of heart rate (HR). Left ventricular pressure was measured with a Millar catheter and $dP/dt_{max}$ was derived. A right thoracotomy was performed and myocardial contractile force (CF) was measured with a Walton Brodie strain gauge sutured to the right ventricle. The ventricular muscle was stretched to produce a baseline tension of 100 g. A standard dose of dopamine (10-15 ug/kg/min for 3 minutes) was administered to determine myocardial responsiveness to inotropic stimulation.

Test compounds were solubilized in a small volume of DMF diluted to a final concentration of 10% in physiological saline. Alternatively, where possible, a soluble hydrochloride salt was prepared by addition of 0.1N HCl diluted in physiological saline. Vehicles were tested in appropriate volumes and found to exert less than a 5% effect on contractile force. For iv studies, compounds were administered by infusion pump (one drug per animal) at rates of 0.50-2.2 mL/minute in three to four stepwise increasing doses. Each dose was infused over 5 minutes immediately after the effect of the previous dose peaked. MAP, HR, $dP/dt_{max}$ and CF responses were continuously monitored on a Beckman or Gould recorder and expressed as a percent change from predrug control values vs. the cumulative dose of drug administered. For these studies, n represents the number of test animals used.

Quantitation of the inotropic potency was obtained by calculation of the contractile force (CF) $ED_{50}$. This was defined as the dose of compound that produced a 50% increase above baseline in myocardial contractile force. The value was obtained from three to four point dose-response curves using either graphical estimation (n<3) or linear regression analysis (@≧3). Data from this evaluation is shown in Table 1. Numbers in parentheses are number of animals screened.

TABLE 1

Cardiovascular Activity of Compounds of the Invention

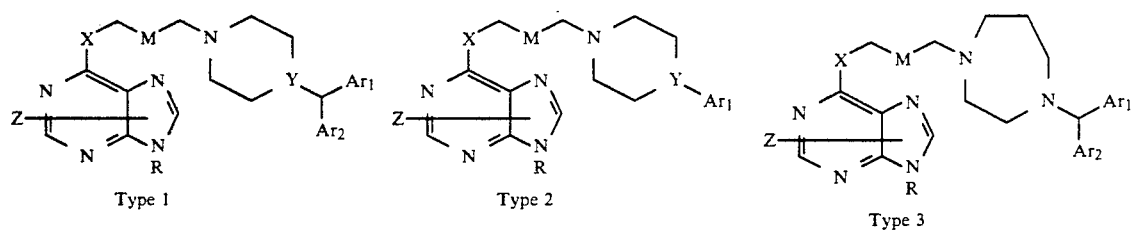

Type 1  Type 2  Type 3

| Example | X | Type | Ar$_1$ | Ar$_2$ | Y | M | Z | R | Dose mpk | MAP | HR | dP/dt | CF |
|---|---|---|---|---|---|---|---|---|---|---|---|---|---|
| 2 | S | 1 | p-FPh | p-FPh | N | CHOSO$_3$H | H | H | 1.875(2) | 6 | 6 | 110 | 159 |
| 4 | S | 1 | p-FPh | p-FPh | N1-oxide | CHOAc | H | H | 1.875(1) | −2 | 3 | 65 | 90 |
| 5 | S | 1 | p-FPh | p-FPh | N1-oxide | CHOH | H | H | 1.875(1) | −2 | 2 | 21 | 43 |
| 6 | S | 1 | p-FPh | p-FPh | N4-oxide | CHOH | H | H | 1.875(1) | 7 | 13 | 36 | 40 |
| 7 | S | 3 | p-FPh | p-FPh | CH2N | CHOAc | H | H | 1.875(1) | −5 | 2 | 18 | 16 |
| 8 | S | 2 | 2-pyridyl | — | N | CHOAc | H | H | 1.875(1) | −11 | 0 | 4 | 43 |
| 9 | S | 2 | 2-pyridyl | — | N | CHOH | H | H | 1.875(1) | −8 | 9 | 27 | 76 |
| 10 | S | 2 | o-MeOPh | — | N | CHOH | H | H | 1.875(2) | −24 | 22 | 54 | 72 |
| 11 | S | 2 | o-MeOPh | — | N | CHOAc | H | H | 1.875(1) | −27 | 35 | 12 | 60 |

The following procedures may be used to prepare reactants which are useful for preparing the compounds of the present invention using the procedures described in the Examples above.

PROCEDURE 1

3-[4-[Bis(4-fluorophenyl)methyl]-1-piperazinyl]-1,2-propanediol.0.25 Hydrate

To a stirred and warmed solution of 4-fluorobenzhydrylpiperazine (6.343 g, 22 mmol) in MEOH (75 mL), a solution of glycidol (1.63 g, 22 mmol) in MEOH (25 mL) was added slowly under nitrogen. The mixture was stirred at room temperature for 18 hours, refluxed for 2 hours and evaporated to dryness. CH$_2$Cl$_2$ (4×100 mL) was added to the syrupy residue and the mixture was evaporated to dryness. The syrupy residue was purified by chromatography on a silica gel column (medium pressure). Eluting with 2%–5% MeOH//CH$_2$Cl$_2$ gave the title compound as a colorless syrup which upon prolonged evacuation formed a hygroscopic foam (5.84 g, 73%), mp 40°–50° C. IR (KBr) cm$^{-1}$: 3625, 3575; $^1$H NMR (CDCl$_3$) δ: 6.9–7.4 (m, 8H, Ar—H); 4.21 [s, 1H, CH(O)$_2$], 3.80 (m, 1H, HCOH), 3.73 and 3.49 (each m, each 1H, HOCH$_2$)3.8–2.3 (m, 10H, N—CH$_2$); MS (DCI): 363 (MH)+.

Anal. Calcd. for C$_{20}$H$_{24}$F$_2$N$_2$O$_2$.¼ H$_2$O: C, 65.46; H, 6.73; N, 7.63 Found: C, 65.09; H, 6.66; N, 7.49.

PROCEDURE 2

3-[4-(Diphenylmethyl)-1-piperazinyl]-1,2-propanediol

In a procedure analogous to that of Procedure 1 above, 4-benzyhydrylpiperazine (12.61 g, 0.05 mmol) in MeOH (50 mL) was reacted with glycidol (3.704 g, 0.05 mmol) in MEOH (20 mL) and worked up to give the title compound as a colorless crystalline solid, 13.20 g (81%), mp 130°–131° C. (mp 125°–126° C. reported by M. Verderame, *J. Med. Chem.*, 11, 1090 (1968)).

Anal. Calcd. for C$_{20}$H$_{26}$N$_2$O$_2$: C, 73.59; H, 8.03; N, 8.58 Found: C, 73.32; H, 8.21; N, 8.48.

PROCEDURE 3

1-(1-Chloro-2-hydroxy-3-propanyl)-4-[bis(4-fluorophenyl)methyl]piperazine Monohydrate To a mixture of epichlorohydrin (3.5 ML, 0.05 mol) in ethanol (12 mL) at 0° C. (ice bath) and anhydrous NaHCO$_3$ (4.2 g, 0.05 mol) [bis(4-fluorophenyl)methyl]piperazine (14.4 g, 0.05 mol) in ethanol (200 mL) was added dropwise over 45 minutes under N$_2$. The ice bath was removed and the mixture was allowed to come to room temperature. After 18 hours the NaHCO$_3$ was removed by filtration via a sintered glass funnel and the ethanol in the filtrate was removed in vacuo to give the crude product (21.3 g). Silica gel flash chromatography using 2.0% MeOH:CH$_2$Cl$_2$ gave pure product (10.05 g, 52.9%) as an amber oil. DCI/MS (M+1) 381. 400 MHz $^1$H NMR (CDCl$_3$) δ: 7.3 (m, 4H), 6.95 (m, 4H), 4.2 (s, 1H), 3.95 (m, 1H), 3.55 (m, 2H), 2.7 (m, 2H), 2.5 (m, 4H), 2.4 (m, 4H).

Anal. Calcd. for C$_{20}$H$_{23}$ClF$_2$N$_2$O.H$_2$O: C, 60.22; H, 6.32; N, 7.02 Found: C, 60.29; H, 6.21; N, 6.83.

PROCEDURE 4

1-(1-Chloro-2-hydroxy-3-propanyl)-4-(diphenylmethyl)piperazine

To a mixture of epichlorohydrin (5.1 mL, 0.065 mL) in ethanol (13 mL) and anhydrous NaHCO$_3$ (0.065 mol, 5.46 g) at 0° C., diphenylmethylpiperazine (16.4 g, 0.065 mol) in ethanol (250 mL) was added dropwise over 45 minutes at room temperature under N$_2$. After 17 hours the NaHCO$_3$ was removed by filtration via a sintered glass funnel and the ethanol was removed from the filtrate in vacuo giving a white-yellow solid (21.5 g). This solid after trituration with Et$_2$O (300 mL) gave a precipitate which was filtered and dried in vacuo to give the pure product (5.11 g, 22.8%) mp 114°–116° C. DCI/MS (M+1) 345. 400 MHz $^1$H NMR (CDCl$_3$) δ: 7.2–7.4 (m, 10H), 4.2 (s, 1H), 3.9 (m, 1H), 3.55–3.7 (m, 2H), 2.7 (m, 2H), 2.45 (m, 8H).

Anal. Calcd. for C$_{20}$H$_{25}$ClN$_2$N$_2$O: C, 69.60; H, 7.20; N, 8.10 Found: C, 69.59; H, 7.44; N, 7.96.

PROCEDURE 5

1-(1-Chloro-2-hydroxy-3-propanyl)-4-benzylpiperazine

To a mixture of epichlorohydrin (3.92 mL, 50 mmol) in EtOH (25 mL) and anhydrous NaHCO$_3$ (4.2 g, 50 mmol) 1-benzylpiperazine (8.66 mL, 50 mmol) in ETOH (100 mL) was added dropwise over 30 minutes at 0° C. under nitrogen. After 16 hours the ETOH was removed in vacuo and the crude product was eluted through silica gel (5% MeOH:CH$_2$Cl$_2$) to give pure product (10.12 g, 75.3%) as an amber oil. DCI/MS (M+1) 269. 400 MHz $^1$H NMR (CDCl$_3$) δ: 7.3 (m, 5H), 4.95 (m, 1H), 4.5 and 4.6 (m, 2H), 3.95 (m, 1H), 3. 6 (m, 2H), 3.5 (s, 2H), 2.7 (m, 4H), 2. 4 (m, 4H).

Anal. Calcd. for C$_{14}$H$_{21}$ClN$_2$O: C, 62.50; H, 7.87; N, 10.40 Found: C, 62.41; H, 7.83; N, 10.35.

PROCEDURE 6

1-(1-Chloro-2-hydroxy-3-propanyl)-4-piperonylpiperazine

To a mixture of epichlorohydrin (3.9 mL, 50 mmol) in ETOH (25 mL) and anhydrous NaHCO$_3$ (4.2 g, 50 mmol) 1-piperonylpiperazine (11.0 g, 50 mmol) in ETOH (125 mL) was added dropwise over 45 minutes at 0° C., under nitrogen. After 16 hours and removal of the ETOH in vacuo, the crude material was passed through silica gel (vacuum, 5% MeOH:CH$_2$Cl$_2$) to give pure product (3.85 g, 26.4%) as an amber oil. DCI/MS (M+1) 313. 400 MHz $^1$H NMR (CDCl$_3$) δ: 7.25 (s, 1H), 6.7–6.8 (m, 2H), 5.9 (s, 2H), 4.6 (m, 1H), 3.9 (m, 1H), 3.5 (m, 2H), 3.4 (s, 2H), 2.4–2.7 (m, 10H).

Anal. Calcd. for C$_{15}$H$_{21}$N$_2$O$_3$Cl: C, 57.59; H, 6.77; N, 8.95 Found: C, 57.241, H, 6.84; N, 8.73.

PROCEDURE 7

1-(1-Chloro-2-hydroxy-3-propanyl)-4-(4-chlorobenzhydryl)piperazine Hemihydrate To a mixture of epichlorohydrin (3.92 mL, 50 mmol) in ethanol (25 mL) and NaHCO$_3$ (4.2 g, 50 mmol) 4-chlorobenzhydryl piperazine (14.34 g, 50 mmol) in ETOH (150 mL) was added dropwise over 45 minutes at 0° C. under nitrogen. After 20 hours, the ETOH was removed in vacuo and the residue was eluted through silica gel using 50% MeOH:CH$_2$Cl$_2$ to give the pure product (3.40 g, 18.3%) as a white solid, mp 72°–74° C. DCI/MS (M+1) 379. 400 MHz $^1$H NMR (CDCl$_3$) δ: 7.5–7.35 (m, 9H), 4.2 (s, 1H), 3.65 (m, 2H), 2.9 (m, 2H), 2.7–2.6 (m, 8H).

Anal. Calcd. for C$_2$OH$_{24}$Cl$_2$N$_2$O.½ H$_2$O: C, 61.80; H, 6.44; N, 7.20 Found: C, 61.67; H, 6.37; N, 7.10.

PROCEDURE 8

1-(1-Chloro-2-hydroxy-3-propanyl)-4-[bis(4-chlorophenyl)methyl]piperazine 4,4'-Dichlorobenzhydrylpiperazine (6.0 g, 18.7 mmol) was reacted as above with epichlorohydrin to give the title compound as an amber oil, 3.67 g (49.8%). 100 MHZ $^1$H NMR (CDCl$_3$) δ: 7.3 (s, 8H), 4.2 (s, 1H), 3.9 (m, 1H), 3.6 (d, 2H, J=10 Hz), 2.9 (m, 2H), 2.7–2.4 (m, 10H).

PROCEDURE 9

1-(1-Chloro-2-hydroxy-3-propoxy)-4-carbethomminerazine Hemihydrate

Carbethoxypiperazine (7.28 mL, 50 mmol) was reacted as above with epichlorohydrin to give the title compound as a clear oil, 8.69 g (69.3%). DCI/MS (M+1) 251. 400 MHZ $^1$H NMR (CDCl$_3$) δ: 4.15 (q, 2H, J=7.1 Hz), 3.9 (m, 1H), 3.6 (m, 2H), 3.5 (m, 4H), 2.6–2.4 (m, 4H), 2.5 (d, 2H, J=6.5 Hz), 1.25 (t, 3H, J=7.11 Hz).

Anal. Calcd. for C$_{10}$H$_{19}$ClN$_2$O$_3$.½ H$_2$O: C, 46.24; H, 7.76; N, 10.78 Found: C, 46.58; H, 7.47; N, 10.65.

PROCEDURE 10

1-(1-Chloro-2-hydroxy-3-propanyl)-4-[bis(3,4'-trifluoromethyl)methyl]piperazine.5/4 Hydrate 3,41-Trifluoromethylphenylpiperazine (1.7 g, 4.4 mmol) was reacted as above with epichlorohydrin to give the title compound as an amber oil, 1.23 g (72%). DCI/MS (M+1) 481. 400 MHz $^1$H NMR (CDCl$_3$) δ: 7.68 (s, 1H), 7.6–7.4 (m, 7H), 4.39 (s, 1H), 3.9 (m, 1H), 3.55 (m, 2H), 2.7 (m, 2H), 2.55–2.4 (m, 8H).

Anal. Calcd. for C$_{22}$H$_{23}$ClF$_6$N$_2$O.5/4H$_2$O: C, 52.54; H, 5.11; N, 5.57 Found: C, 52.48; H, 5.41; N, 5.22.

PROCEDURE 11

1-(1-Chloro-2-hydroxy-3-propanyl)-4-(triphenylmethyl)piperazine.¼ Hydrate 1-(Triphenylmethyl)piperazine (5.25 g, 16 mmol) was reacted as above with epichlorohydrin to give the title compound as a white solid, 2.79 g (41.4%), mp 91°–94° C. DCI/MS (M+1) 421. 400 MHz $^1$H NMR (CDCl$_3$) δ: 7.5–7.15 (m, 15H), 3.86 (m, 1H), 3.52 (d, 2H, J=4.85 Hz), 2.9 (m, 2H), 2.8–2.4 (m, 10H).

Anal. Calcd. for C$_{26}$H$_{29}$ClN$_2$O.¼ H$_2$O: C, 73.39; H, 6.99; N, 6.58 Found: C, 73.34; H, 6.83; N, 6.53.

PROCEDURE 12

Bis(4-chlorophenyl)chloromethane

To 4-chlorobenzhydrol (12.66 g, 50 mmol) in CH$_2$Cl$_2$ (200 mL) under nitrogen, thionyl chloride (10 mL, 137 mmol) was added dropwise over 15 minutes. After 18 hours and removal of the solvent in vacuo, the crude product was dissolved in CH$_2$Cl$_2$ (100 mL) and washed with saturated NaHCO$_3$ (3×), dried over Na$_2$SO$_4$, and concentrated in vacuo to a thin, amber oil (12.53 g). Upon standing at room temperature for 1 hour, crystallization occurred to give pure product (12.5 g, 88.4%) as a white solid, mp 61°–64° C. DCI/MS (M+1) 235. 400 MHz $^1$H NMR (CDCl$_3$) δ: 7.35 (m, 8H), 6.05 (s, 1H).

Anal. Calcd. for Cl$_3$H$_9$Cl$_3$: C, 57.49; H, 3.34 Found: C, 57.69; H, 3.46. This is a known compound: *Chem. Abstract.*, 1957, 51, 9717a.

To piperazine (9.15 g, 106 mmol) in CHCl$_3$ (200 mL) containing potassium iodide (2.66 g, 16 mmol) under a nitrogen atmosphere bis(4-chlorophenyl)chloromethane (9.5 g, 35 mmol) in CHCl$_3$ (100 mL) was added dropwise with stirring over a period of 45 minutes. After 6 days, the reaction mixture was filtered, concentrated and the crude product was purified by flash chromatography using 10% MEOH in CH$_2$Cl$_2$ to give the title compound as a thick amber oil. 400 MHz $^1$H NMR (CDCl$_3$) δ: 7.25 (M, 8H), 4.25 (s, 1H), 2.9 (m, 4H), 2.3 (m, 4H).

PROCEDURE 13

6-Chloro-9-(tetrahydro-2-pyranyl)purine

To a warmed (60° C.) slurry of 6-chloropurine (20 g, 0.1294 mol) and R-toluenesulfonic acid monohydrate (0.35 g), dihydropyran (13.4 mL, 0.172 mol) was added with stirring over a period of 30 minutes. After an additional 30 minutes of heating, the mixture was allowed to cool to room temperature for 1 hour. Concentrated ammonium hydroxide (12 mL) was added and stirring was continued for 5 minutes. The solution was washed with water (4×70 mL) and the organic layer was dried (Na$_2$SO$_4$), filtered and concentrated in vacuo to give a syrup (about 29 g) which slowly crystallized upon standing. Extraction with boiling hexane gave the product as a solid, 24.36 g in two crops (78%), mp 70°–71° C.

Anal. Calcd. for $C_{10}H_{11}ClN_4O$: C, 50.32; H, 4.65; N, 23.47 Found: C, 50.25; H, 4.59; N, 23.25. This is a known compound: R. K. Robins et al, *J. Amer. Chem. Soc.*, 83, 2574 (1961).

PROCEDURE 14

1-(1-Chloro-3-propanyl)-4-[bis(4-fluorophenyl)methyl]-piperazine

Pentane (10 mL) was added to sodium hydride(0.50 g, 11 mmol of 50% suspension in mineral oil) and the mixture was stirred under nitrogen. The pentane was decanted. Anhydrous DMF (12 mL) was added and the suspension was cooled to 0° C. [Bis(4-fluorophenyl)methylpiperazine (2.9 g, 10 mmol) in anhydrous DMF (14 mL) was added at 0° C. within 10 minutes. The reaction mixture was allowed to warm to room temperature. After 1 hour, the mixture was cooled to 0° C. and to the light green solution 1-chloro-3-bromopropane (5 mL, 50 mmol) in anhydrous DMF (5 mL) was added over a period of 10 minutes. The mixture was stirred under nitrogen at room temperature for 72 hours. The solvents were evaporated in vacuo (1 mm Hg) at 50° C. The residue was triturated in methylene chloride and filtered through Celite ®. The filtrate was washed with water (2 × 100 mL), dried (sodium sulfate), filtered, and the filtrate was evaporated in vacuo to give crude chloro-propyl compound (3.65 g). Pentane (50 mL) was added, and on the next day the pentane insoluble solid was removed by filtration. The filtrate was evaporated in vacuo to give the title compound (2.3 g, 75%) as a clear, colorless oil. 100 MHz $^1H$ NMR (CDCl₃) δ: 7.32 (m, 4H), 6.95 (m, 4H), 4.2 (s, 1H), 3.57 (m, 2H), 2.2–2.6 (m, 10H), 1.9 (m, 2H). DCI/MS (M+1) 361.

Anal. Calcd. for $C_{20}H_{23}ClF_2N_2$: C, 65.83; H, 6.35; N, 7.68 Found: C, 65.59; H, 6.42; N, 7.63.

PROCEDURE 15

1-[1-(2,3-Epoxy)propyl]-4-[bis(4-fluorophenyl)methyl-piperazine

A solution of 4,4'-difluorobenzhydrylpiperazine (28.83 g, 100 mmol) in acetonitrile (250 mL) was added to an ice cold mixture of epibromohydrin (9.1 mL, 110 mmol) and anhydrous potassium carbonate (15.2 g, 110 mmol) in acetonitrile (150 mL) over a period of 40 minutes. The mixture was stirred at room temperature for 100 hours, filtered and the solids were washed with methylene chloride. The combined filtrates were concentrated to dryness to give an oil which was eluted through a flash chromatographic silica gel column using 2–3% methanol/methylene chloride to give the title compound as glass, 23.98 (69.6%) ; 300 MHz $^1H$ NMR (CDCl₃): δ: 7.4–6.9 (m, 8H), 4.22 (s, 1H), 3.09 (br M, 1H), 2.8–2.25 (m, 12H); MS 345 (MH⁺).

Anal. Calcd. for $C_{20}H_{22}F_2N_2O$: C, 69.75; H, 6.44; N, 8.13; F, 11.50 Found: C, 69.73; H, 6.49; N, 8.19; F, 11.66.

PROCEDURE 16

1-Amino-3-[4-[bis(4-fluorophenyl)methyl]-1-piperazinyl]-2-propanol

A solution of 1-[1-(2,3-epoxy)propyl]-4-[bis-(4-fluorophenyl)methyl]piperazine (8.9 g, 25.8 mmol) from Procedure 17, and liquid ammonia (20 mL) in ETOH (40 mL) was heated in a Teflon ® reaction vessel in a bomb at 110° C. for 28 hours. The solution was then evaporated to dryness to give about 10 g of a glass which was purified using flash chromatography on silica gel and increasing proportions of methanol in methylene chloride to give the product as an oil which solidified upon vacuum drying, 5.7 g (61%), mp 45°–47° C. IR(neat) 3350 cm⁻¹; 300 MHz $^1H$ NMR (CDCl₃): δ: 7.4–6.9 (m, 8H), 4.21 (s, 1H), 3.68 (br m, 1H), 2.8–2.2 (m, 12H); MS 362 (MH⁺).

Anal. Calcd. f or $C_{20}H_{25}F_2N_3O$: C, 66.46; H, 6.97; N, 11.63 Found: C, 66.21; H, 7.10; N, 11.63.

What is claimed is:

1. A compound of the formula:

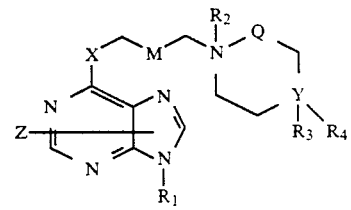

and optically active isomers thereof;
wherein:
R₁ represents hydrogen, $C_{1-4}$alkyl, cyclopentyl, cyclohexyl, benzyl, $C_{2-6}$alkenyl, $C_{2-6}$alkynyl, tetrahydropyranyl, or tetrahydrofuranyl;

R₂ and R₃ individually represent oxygen or no substituent;

R₄ represents naphthyl, pyridyl, thienyl, CHR₅R₆, or CR₅R₆ when Y represents C=, phenyl or substituted phenyl wherein the substituent is $C_{1-4}$alkyl, $C_{1-4}$alkoxy, CF₃, halo, perhalo, NO₂, or CN;

R₅ and R₆ individually represent naphthyl, pyridyl, thienyl, phenyl or substituted phenyl wherein the substituent is $C_{1-4}$alkyl, $C_{1-4}$alkoxy, CF₃, halo, perhalo, NO₂, or CN;

Z represents hydrogen, CN, $C_{1-4}$alkyl, halo, hydroxy, amino, or CO₂R₇ wherein R₇ represents hydrogen, $C_{1-4}$alkyl, NO₂, halo, CN, or CF₃;

X represents S, O, NH, or NR₈ wherein R₈ represents $C_{1-4}$alkyl;

M represents CH₂, CHOH, CHOCOR₉, or CHOR₉ wherein R₉ represents straight or branched chain $C_{1-4}$alkyl, SO₃H, phenyl, or substituted phenyl wherein the substituent on the phenyl is $C_{1-4}$alkoxy, NO₂, or CN;

Q represents CH₂ or (CH₂)₂; and

Y represents nitrogen or a carbon atom having a double bond (C=) when R₄ is CR₅R₆;

with the provisos that:
(a) when Y is N and R₄ is any substituent other than CR₅R₆, X is S or O;
(b) When R₄ is CHR₅R₆ or CR₅R₆, at least one of R₂ and R₃ must be oxygen; or
(c) when R₄ is CHR₅R₆ or CR₅R₆, at least one of R₅ and R₆ is an aromatic group; and
(d) R₃ can be oxygen only when Y is nitrogen.

2. A compound of claim 1 wherein Q is (CH₂)₂.

3. A compound of claim 1 wherein R₂ is oxygen.

4. A compound of claim 1 wherein R₃ is oxygen.

5. A compound of claim 1 wherein R₄ is a substituent selected from the group consisting of naphthyl, pyridyl, thienyl, CHR₅R₆, phenyl or substituted phenyl wherein the substituent is $C_1$–$C_4$ lower alkyl, $C_1$–$C_4$ lower alkoxy, CF₃, halo, perhalo, NO₂ or CN.

6. A compound of claim selected from the group consisting of 6-[1-[1-[bis(4-fluorophenyl)methyl)piperazin-1-N-oxide-4-yl]-2-acetoxy-3-propanylthio]purine monohydrate, 6-[1-[1-bis(4-fluorophenyl)methyl]piperazin-1-N-oxide-4-yl]-2-hydroxy-3-propanylthio]purine monohydrate and 6-[1-[1-[bis(4-fluorophenyl)methyl]-piperazin-4-N-oxide-4-yl]-2-hydroxy-3-propanylthio]-purine hydrate.

7. A compound of claim 1 selected from the group consisting of 6-[1-[1-[2-pyridyl]piperazin-4-yl]-2-acetoxy-3-propanylthio]purine hemihydrate, 6-[1-[1-[2-pyridyl)piperazin-4-yl]-2-hydroxy-3-propanylthio]purine monohydrate, 6-[1-[1-(2-methoxyphenyl)piperazin-4-yl]-2-hydroxy-3-propanylthio]purine and 6-[1-[1-(2-methoxyphenyl)piperazin-4-yl]-2-acetoxy-3-propanylthio]purine.

8. A pharmaceutical composition comprising as an active ingredient an effective amount of a compound of claim 1, and a suitable pharmaceutical carrier.

9. A pharmaceutical composition comprising as an active ingredient an effective amount of a compound of claim 2, and a suitable pharmaceutical carrier.

10. A pharmaceutical composition comprising as an active ingredient an effective amount of a compound of claim 3, and a suitable pharmaceutical carrier.

11. A pharmaceutical composition comprising as an active ingredient an effective amount of a compound of claim 4, and a suitable pharmaceutical carrier.

12. A pharmaceutical composition comprising as an active ingredient an effective amount of a compound of claim 5, and a suitable pharmaceutical carrier.

13. A pharmaceutical composition comprising as an active ingredient an effective amount of a compound of claim 6, and a suitable pharmaceutical carrier.

14. A pharmaceutical composition comprising as an active ingredient an effective amount of a compound of claim 7, and a suitable pharmaceutical carrier.

15. A method of treating heart disease in mammals by administering an effective amount of a compound of claim 1.

16. A method of treating heart disease in mammals by administering an effective amount of a compound of claim 2.

17. A method of treating heart disease in mammals by administering an effective amount of a compound of claim 3.

18. A method of treating heart disease in mammals by administering an effective amount of a compound of claim 4.

19. A method of treating heart disease in mammals by administering an effective amount of a compound of claim 5.

20. A method of treating heart disease in mammals by administering an effective amount of a compound of claim 6.

21. A method of treating heart disease in mammals by administering an effective amount of a compound of claim 7.

* * * * *

UNITED STATES PATENT AND TRADEMARK OFFICE
CERTIFICATE OF CORRECTION

PATENT NO. : 5,252,569
DATED : October 12, 1993
INVENTOR(S) : Zoltan G. Hajos, et al.

It is certified that error appears in the above-indentified patent and that said Letters Patent is hereby corrected as shown below:

Col. 19, line 1, insert --1-- after "claim"

Signed and Sealed this

Seventh Day of June, 1994

*Attest:*

BRUCE LEHMAN

*Attesting Officer*   *Commissioner of Patents and Trademarks*